United States Patent [19]

Sartore

[11] Patent Number: 4,777,364

[45] Date of Patent: Oct. 11, 1988

[54] DEFECT DETECTION AND THICKNESS MAPPING OF THE PASSIVATION LAYER(S) OF INTEGRATED CIRCUITS

[75] Inventor: Richard G. Sartore, Bradley Beach, N.J.

[73] Assignee: The United States of America as represented by the Secretary of the Army, Washington, D.C.

[21] Appl. No.: 61,626

[22] Filed: Jun. 15, 1987

[51] Int. Cl.[4] ............................................. G01N 23/225
[52] U.S. Cl. .................................... 250/307; 250/310; 250/306
[58] Field of Search ...................... 250/306, 307, 310; 378/50, 89

[56] References Cited

U.S. PATENT DOCUMENTS 3,376,419 4/1968 Schumacher ..................... 250/307

OTHER PUBLICATIONS

Conference on "Scanning Electron Microscopy", Techniques for Sectioning Microcircuit Metallization, Hackett, 1976, pp. 579-586.
"Determination of KeV Electron Energy Dissipation vs. Penetration Distance in Solid Materials", by T. E. Everhart and P. H. Hoff, Journal of Applied Physics, vol. 42, No. 13, Dec. 1971, pp. 5837-5846.

Primary Examiner—Carolyn E. Fields
Assistant Examiner—John A. Miller
Attorney, Agent, or Firm—Sheldon Kanars; John K. Mullarney

[57] ABSTRACT

A narrow, high energy, electron beam is caused to impinge upon an integrated circuit. The accelerating voltage of the electron beam is increased until the electrons have just enough energy to penetrate through the thickness of the passivation layer ($SiO_2$). The accelerating voltage is then increased a predetermined amount (3-5 KeV) above the voltage required for passivation layer penetration. The transmitted electrons interact with the sublayer of film material (Al) to generate distinct X-rays. The increased-intensity electron beam is x/y or raster scanned over the area of interest of the IC chip. The X-ray intensities generated during the raster scan are detected and stored (e.g., in a RAM). After a complete scan of the area of interest, the X-ray intensities are read out of store and visually displayed on a CRT. Through correlation of measured and predicted X-ray intensities, a scanning thickness mapping is available for display/quantitative analysis of the thickness profile of a passivation layer.

9 Claims, 4 Drawing Sheets

DEFECT DETECTION AND THICKNESS MAPPING OF THE PASSIVATION LAYER(S) OF INTEGRATED CIRCUITS

The invention described herein may be manufactured, used, and licensed by the Government for governmental purposes without the payment to me of any royalties thereon.

TECHNICAL FIELD

The present invention relates to a method of detecting defects and mapping the thickness of the passivation layer(s) of integrated circuits using an energy dispersive X-ray analysis (EDXA) technique.

BACKGROUND OF THE INVENTION

To perform failure analysis and process evaluation on the silicon dioxide passivation (i.e., insulation) layer(s) used in microelectronic devices (IC chios), the ability to detect defects in the layer(s) is required. Typically, holes or thickness non-uniformity in a passivation layer can cause device failure or electrical malfunction. These defects can be a micron in size or larger and need to be detected/localized over a relatively large area. Due to the random nature of the defects, the holes in the insulation can occur any place over the metallization run (i.e., the entire etched IC film surface), which, of course, would cause a failure. Besides hole defects, a thinning/non-uniformity of the passivation/insulation layer over/under/adjacent to high field regions of the IC chip can be a potential failure site, or can substantially degrade the device's electrical performance. Accordingly, a high degree of characterization of the insulating layer is desirable for process evaluation and production monitoring. That is, the ability to accurately characterize (i.e., defect detect and thickness map) the passivation/insulating layer(s) both during and after device processing is of substantial importance to ultimate device yield and device electrical performance.

SUMMARY OF THE INVENTION

It is the primary object of the present invention to achieve a method or technique for detecting defects and mapping the thickness of the passivation/insulation layer(s) of integrated circuits which is simple to implement, uses relatively low accelerating electron beam voltages, and yet achieves a high degree of layer characterization.

A related object is to accurately characterize the passivation/insulating layer(s) of integrated circuits in a relatively fast, yet non-destructive manner.

In accordance with the invention, a penetration voltage method is used to determine the energy required by an electron beam to penetrate the passivation layer. In this method, an accelerating electron beam voltage is varied until the electrons have just enough energy to penetrate through the thickness of the layer. Then, in accordance with the invention, the accelerating voltage is increased a predetermined amount (i.e., at least 3 KeV) so that the electron beam penetrates into the integrated circuit thin film (e.g., A1) and thereby interacts with the sublayer or film material to generate X-rays. These X-rays are detected by an energy dispersive X-ray analyzer (EDXA). The increased-intensity electron beam is then x/y or "raster" scanned over the area of the film and the generated X-ray intensity at each pixel is stored and then raster displayed on a cathode ray tube (CRT), for example. If the insulating layer on top has a non-uniform thickness, it will show-up as a thickness modulated intensity variation of the characteristic X-ray from the sublayer or film material. By X-ray mapping the X-rays from the sublayer material for the area of interest of a microelectronic device, it is possible to visually find a hole defect or thickness non-uniformity uniformity defect in the insulation over the metallization. Once a defect area is detected using X-ray mapping, it can be more thoroughly analyzed by using X-ray linescan or spot mode analysis.

It is an advantageous feature of the invention that it is equally applicable to multi-level metal devices. Since multi-level metallization has become an increasingly popular solution for use in VHSIC/VLSI device designs, a very high degree of characterization of the several insulating layers is desirable for process evaluation and continual process monitoring. Briefly, after each metallization and the covering of the same by a passivation layer, the method set forth above is carried out. And, the method or process of the invention is repeated for each level of metallization and its insulating layer.

BRIEF DESCRIPTION OF THE DRAWINGS

The invention will be more fully appreciated from the following detailed description when the same is considered in connection with the accompanying drawings, in which.

DETAILED DESCRIPTION

Figure 1:
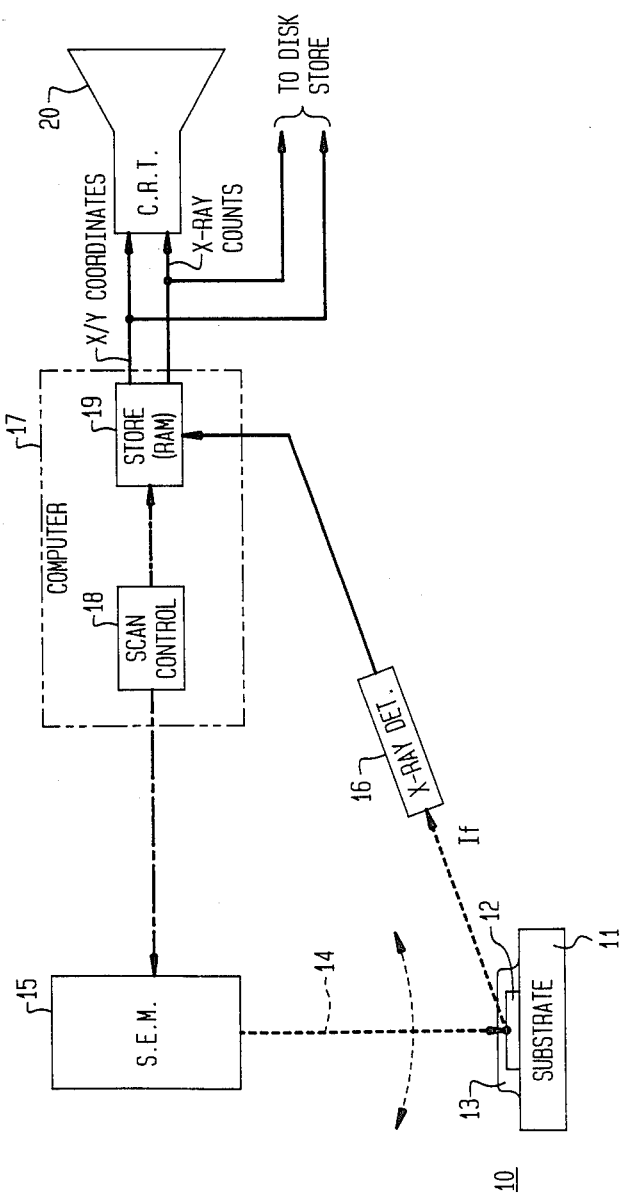
FIG. 1 is a schematic block diagram of the apparatus arrangement used in carrying out the technique of the present invention.

Turning now to FIG. 1 of the drawings, the (enlarged) integrated circuit 10 comprises a substrate 11 (typically silicon), a film 12 of aluminum, for example, which is etched or processed to a particular design specification, and a passivation or insulation layer 13 of say silicon dioxide ($SiO_2$). The layer 13 should preferably be of a specified, uniform thickness and free of defects such as holes. Unfortunately, in practice this is sometimes not the case. It is the purpose of the present invention to detect defects and thickness non-uniformity in this passivation layer and, in particular, holes and a deleterious thinness in the layer. To this end, a narrow, high energy, electron beam 14 is generated by a scanning electron microscope (SEM) 15 and impinges upon the integrated circuit (IC) 10. As is known to those in the art, the electron beam can be directed to a very specific point on the IC chip (+/− one micron). As the accelerating voltage of the electron beam 14 is increased in intensity the electrons will penetrate further into the chip. As a consequence, the transmitted electrons interact with the material(s) of the chip to generate X-rays. These X-rays are then detected by the X-ray detector 16, which is a commercially available item, as of course is the SEM. The X-rays from the passivation layer 13 and from the A1 film 12 are distinct since they are of different wavelengths (λ).

A penetration voltage method is used to determine the accelerating voltage required for passivation layer penetration and, as a corollary, the thickness of the SiO₂ layer at the point of the electron beam impingement. Briefly, in this method, the accelerating voltage of the electron beam 14 is varied (i.e., increased in incremental steps) until the electrons have just enough energy to penetrate the thickness of the SiO₂ layer 13. This penetration voltage method is the subject of applicant's co-pending patent application Ser. No. 043,271, filed Apr. 23, 1987, and entitled "Measurement of Film Thickness of Integrated Circuits". Accordingly, further detailed description herein of this penetration voltage method would not appear to be warranted.

Once the penetration accelerating voltage is determined and, its corollary, the SiO₂ layer thickness is found to be within an acceptable thickness range (e.g., +/− 0.2 microns at 0.7 microns thickness), the electron beam 14 is caused to scan in an x/y "raster" fashion and the energy of the beam is increased. More specifically, and in accordance with the concept of the present invention, the accelerating voltage of the electron beam 14 is increased at least 3 KeV. above the accelerating voltage (e.g., 9 KeV.) required for SiO₂ penetration. In theory, the accelerating beam can, of course, be increased substantially more than 3 KeV. above the penetration accelerating voltage. As a practical matter, however, any very substantial increase above 3 KeV. can damage the A1 film 12, causing the device to malfunction electrically. In practice, an increase in the accelerating voltage in the 3.0–5.0 KeV. range has proven to be satisfactory, with less likelihood of chip damage. Furthermore, if the intensity of the electron beam is increased as indicated (3–5 KeV.), a linear relationship is found to exist between the X-ray intensity (I f) and the (A1) film material and the thickness of the passivation layer (e.g., SiO₂). Thus, the measured (If) X-ray intensity can be used to provide a direct indication of passivation layer thickness. This will be covered in greater detail hereinafter. As previously noted, too great an increase in the accelerating voltage over the layer penetration voltage may result in chip damage; and, too small an increase (e.g., 1.0 KeV.) results in a non-linear relationship between the (If) X-ray intensity and passivation layer thickness.

The computer 17 comprises scan control apparatus 18 and a storage capacity 19, such as a random access memory (RAM or DRAM). The scan control 18 develops the necessary x and y coordinate, or raster scan, signals and these are delivered to the scan coils (not shown) of the SEM 15. In this manner, the increased-intensity electron beam 14 is scanned over the area of interest of the IC chip. For the typical chip, an X-ray map of 128×128 pixels (or points) was found to be satisfactory. The acquisition time at each pixel is preferably 0.01–0.04 seconds. For best resolution of the defects more X-ray counts are desirable and, therefore, an acquisition time of 0.04 sec. is preferable, but the invention is in no way limited thereto. A computer made by Digital Equipment Corp. was used for the stated purpose, but a computer made by any of the other computer manufacturers can be readily used instead.

The x/y raster scan signals generated by the control 18 are also coupled to the store 19, as are the X-ray counts from the scanned pixels. Thus, the stored X-ray counts correspond (spatially) to the X-rays generated by the impingement of the electron beam 14 as it is scanned over the pixels or points of the A1 film of the chip. After storage, the stored raster of X-ray counts is read out and delivered to a display device, such as cathode ray tube (CRT) 20. The CRT will provide a visual X-ray map of the scanned IC chip. If the insulating layer 13 has a defect or a deleterious thinness, it will visually show up as a thickness modulated intensity variation of the characteristic X-rays from the sublayer or film material. Accordingly, by X-ray mapping the X-rays from the sublayer material (A1) of the IC chip, it is now possible to visually detect a hole defect or thinness defect in the insulation over the metallization.

In addition to an immediate visual display, the X-ray map information can also be delivered to a disk store for later evaluation and quantitative analysis as described below. As will be readily apparent to those skilled in the art, all of the apparatus utilized in the arrangement of FIG. 1 are commercially available items.

Figure 2:
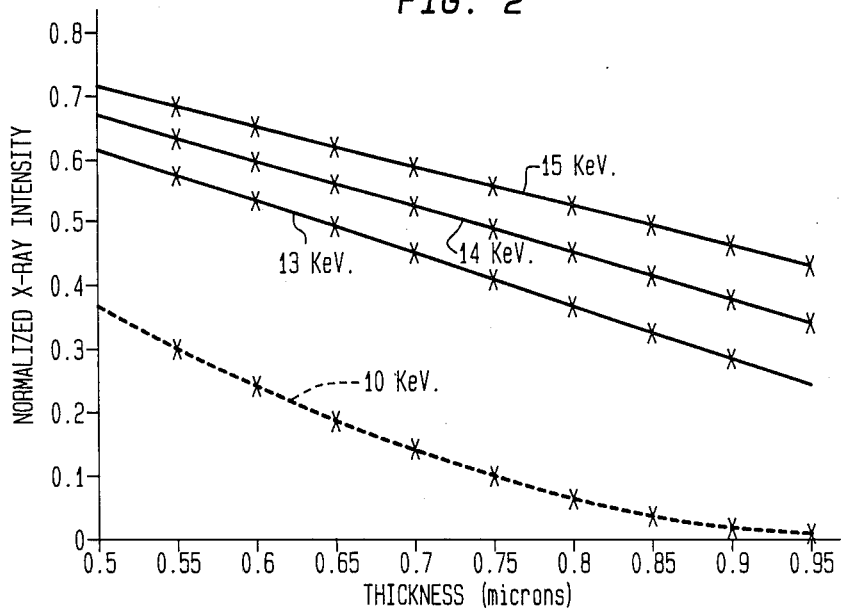
FIG. 2 is a plot of the calculated A1 (K) X-ray intensity from the sublayer for various thicknesses of a silicon dioxide top or insulation layer and with different accelerating voltages of 13-15 KeV.

FIG. 2 is a plot of normalized X-ray intensity (pure, uncoated, aluminum being the norm) from the sublayer 12 for various thicknesses of a silicon dioxide top or insulation layer 13 and with different accelerating voltages. As indicated in FIG. 2, when the electron beam is increased at least 3 KeV. above the penetration accelerating voltage, a substantially linear relationship exists between the normalized X-ray intensity from the film material and the thickness of the passivation layer (see the curves for 13–15 KeV.). Accordingly, the measured normalized (If) X-ray intensity will provide a direct indication of passivation layer thickness. However, too small an increase (e.g., 1.0 KeV) over the penetration accelerating voltage results in a non-linear relationship between the normalized X-ray intensity and passivation layer thickness; see the 10 KeV. dotted curve of FIG. 2.

The curves of FIG. 2 were calculated, the Everhart and Hoff formulation being the basis for the same; see the article entitled "Determination of KeV Electron Energy Dissipation vs. Penetration Distance in Solid Materials" by T. E. Everhart and P. H. Hoff, Journal of Applied Physics, Vol. 42, No. 13, Dec. 1971, pp. 5837–46.

From the Everhart-Hoff formulation, the following intensity (If) equation was derived:

$$I = 1 - 38.5\,(t \cdot E^{-1.75}) - 8318.77\,(t^2 \cdot E^{-3.5}) + 621688.6726\,(t^3 \cdot E^{-5.25}) - 11735723.51\,(t^4 \cdot E^{-7}),$$

where t is the passivation layer thickness and E is the accelerating voltage. The constants were computer derived. Now, knowing the accelerating voltage and the measured normalized X-ray intensity one could presumably go to one of the linear curves of FIG. 2 to determine the layer thickness at a given point. In practice, however, a computer can be readily programmed to utilize the above equation to derive the thickness (t) given the values for E and the measured normalized intensity (I).

Figure 3:
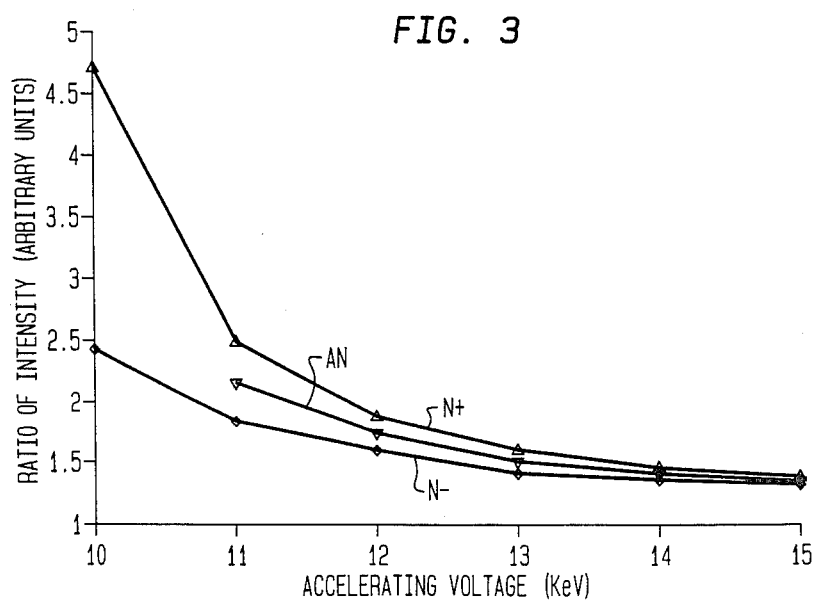
FIG. 3 is a plot of the calculated relative intensity ratio for a thickness variation of 0.2 microns at 0.7 microns for various accelerating voltages.

The relative intensity ratio for a thickness variation equal to 0.2 microns at 0.7 microns was calculated for various acceleration voltages and plotted in FIG. 3. N−, N+ and AN were calculated using data in FIG. 2, where AN is the average of the N− and N+ curves. N− corresponds to the thickness variation from 0.5 to 0.7 microns and N+ to the (0.2μ) variation on the positive side of 0.7 microns. As is shown in FIG. 3, a thickness variation of +/− 0.2 microns at 0.7 microns thickness would be detectable with relatively modest error, using accelerating voltages from 12 keV to 15 KeV, with increasing error as the accelerating voltage is lowered.

Figure 4:
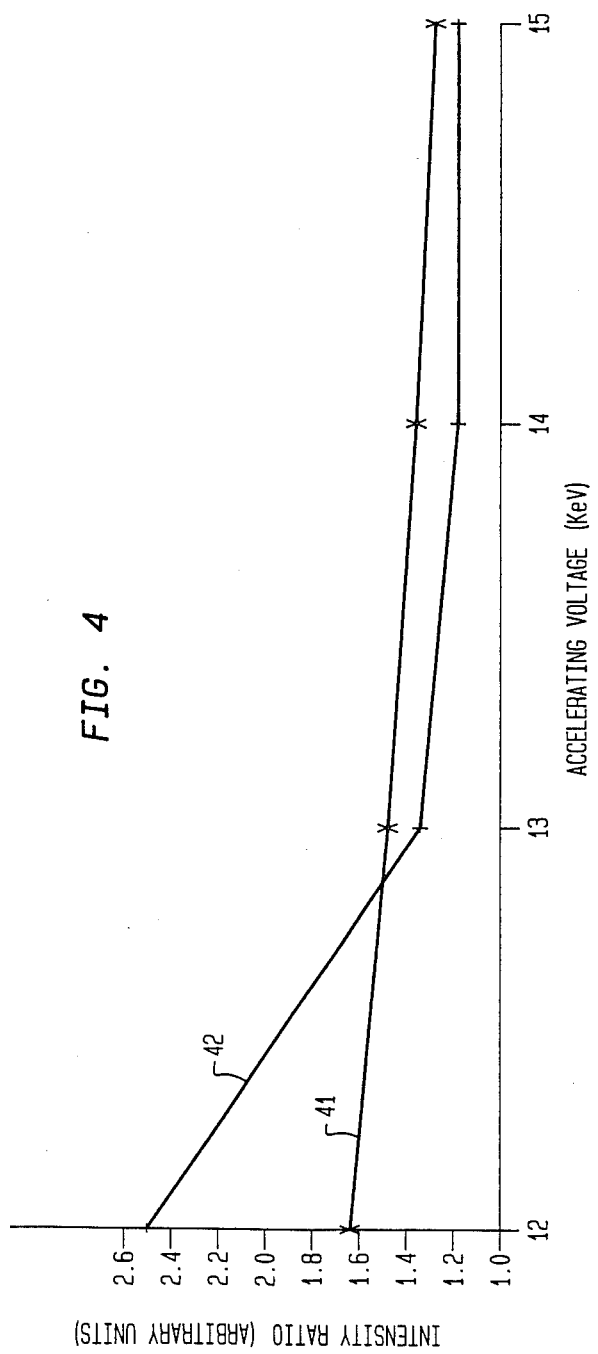
FIG. 4 is a plot of intensity variation vs. accelerating voltage for acquired data and for calculated data.

The curves of FIG. 4 show a measured relative intensity ratio 42 compared to a calculated relative intensity ratio 41 for an assumed thickness variation of 0.2 microns at 0.7 microns, and at different accelerating voltages (12-15 KeV). That is, the calculated curve 41 corresponds to the N− curve of FIG. 3. The curve 42 is the (X-ray) intensity measured at a given point on the film material (A1) relative to the intensity at a reference point (0.7 microns). The calculated curve 41 is the standard against which the measured intensities must be compared. It will be seen that at 13, 14 and 15 KeV the measured relative intensity ratio is close to and less than that of the standard (curve 41) and, as a corollary, the (measured) thickness variation is therefore less than 0.2 microns. This confirms the validity of the measurement techniques of the present invention. It will be seen that at the lower accelerating voltages (<3 KeV over the penetration voltage) the difference between the calculated and measured intensity ratios becomes significant, with the measured curve 42 being significantly greater than the calculated curve 41. Moreover, as the accelerating voltage is lowered even further, the curves of FIG. 4 would diverge even more than shown.

Figure 5:
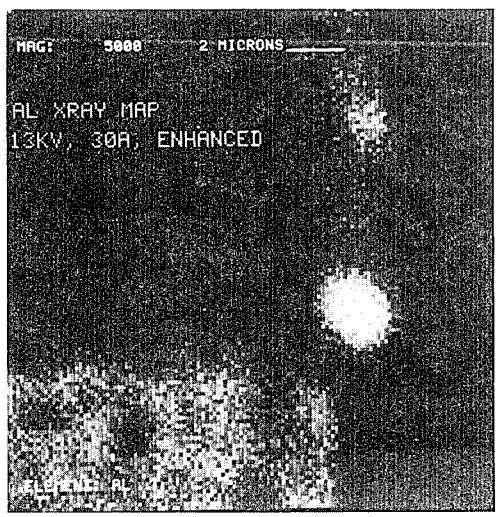
FIG. 5 illustrates a CRT display of an X-ray map in accordance with the invention, the map showing a hole defect and some thinning of the insulating material.

FIG. 5 shows a cathode ray tube display of an X-ray map taken in accordance with the principles of the present invention. The film material was A1, the accelerating voltage was 13 KeV. and the designation 30A indicates a 30 take-off angle. Also, the image was enhanced. The brightened area in the lower, left-to-center section of the map indicates a thinning/non-uniformity of the passivation layer. This may or may not be significant, but clearly it suggests that further examination is called for. The very bright spot slightly off-center (to the lower, right of center) clearly indicates a hole defect which would undoubtedly affect the electrical performance of the IC chip.

To obtain better statistics and measurements after the initial detection and thickness estimation carried out in accordance with the thickness mapping technique, linescans of the area of interest can be acquired. Acquisition of linescan allows the accumulation of better statistics for a shorter time period. A series of linescans at different accelerating voltages can be carried out for an area with a thinning/non-uniformity or hole defect. Alternatively, and particularly for a hold defect, a spot analysis can be done. That is, the store 19 can be accessed to obtain the X-ray count(s) from one or more pixels. The count or counts will provide a thickness indication, as previously described.

To enhance the X-ray images for better visual analysis on the CRT, standard image enhancement techniques were utilized. Scaling, background subtraction and image ratio operations were performed on the acquired X-ray map. Smoothing of the X-ray image is also available and can prove useful for "noisy" images, i.e., images acquired under low count rate conditions. The smoothing function averages the pixels with nearest neighbors to produce a more uniform image when the acquisition is done at too low a count rate.

The utility of the invention was described in terms of its applicability to an integrated circuit comprised of a silicon dioxide layer over an aluminum metallization run. However, as should be obvious to those skilled in the art, the principles of the present invention is not so limited. Clearly, the invention has equal applicability to integrated circuits comprised of other and different passivation layers (e.g., silicon nitride) and other and different film materials (e.g., tungsten). As will be further evident to those in the art, the technique is also equally applicable to thick film as well as thin film integrated circuits.

Having thus shown and described what is at present considered to be the preferred method, it should be understood that the same has been shown by way of illustration and not limitation. Accordingly, all modifications, alterations and changes coming within the spirit and scope of the invention as defined in the appended claims are herein meant to be included.

What is claimed is:

1. A method of detecting defects and mapping the thickness of the passivation layer of an integrated circuit comprising the steps of:
    directing a narrow, high energy, electron beam to impinge upon an integrated circuit;
    increasing the accelerating voltage of the electron beam until the electrons have just enough energy to penetrate through the thickness of the passivation layer;
    increasing said voltage a predetermined amount above the voltage required for passivation layer penetration;
    the transmitted electrons serving to interact with a sublayer of film material to generate distinct X-rays;
    the predetermined amount of voltage increase being sufficient to achieve a substantially linear relationship between the X-ray intensity from the film material and the thickness of the passivation layer;
    raster scanning the increased-intensity electron beam over the area of interest of the integrated circuit;
    detecting said X-rays that are generated during said scanning of the electron beam; and
    visually displaying the X-rays detected during said raster scanning.

2. The method of claim 1 wherein said predetermined amount is at least 3 KeV.

3. The method of claim 2 wherein said predetermined amount is in the 3 to 5 KeV range.

4. A method in accordance with claim 3 wherein the steps are repeated for each level of film material and its passivation layer of a multi-level metal device.

5. The method of claim 3 including the steps of first storing the X-ray intensities detected during said scanning of said electron beam; and
    reading out the stored X-ray intensities and raster displaying the same on a cathode ray tube.

6. The method of claim 5 wherein the accelerating voltage of the electron beam is initially increased in incremental steps of three or more until the passivation layer is penetrated.

7. The method of claim 6 wherein the passivation layer is comprised of silicon dioxide and the film material is etched aluminum.

8. The method of claim 7 wherein a detected normalized X-ray intensity (I) is related to the passivation layer thickness (t) in accordance with the following formula:

$$I = 1 - 38.5 \, (t \cdot E^{-1.75}) - 8318.77 \, (t^2 \cdot E^{-3.5}) + 621688.6726 (t^2 \cdot E^{-5.25}) - 11735723.71 \, (t^4 \cdot E^{-7}),$$

where E is the accelerating voltage.

9. The method of claim 8 wherein the thickness of the passivation layer is mapped over the raster scan area by correlation of measured relative intensity variations to predicted variations, based on experimentally verified model.

* * * * *